United States Patent
Heidemann et al.

(10) Patent No.: US 8,529,869 B2
(45) Date of Patent: Sep. 10, 2013

(54) CATALYSTS AND METHOD FOR THE HYDROAMINATION OF OLEFINS

(75) Inventors: Thomas Heidemann, Viernheim (DE); Jens Kehrer, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 97 days.

(21) Appl. No.: 13/265,457

(22) PCT Filed: Apr. 19, 2010

(86) PCT No.: PCT/EP2010/055078
§ 371 (c)(1),
(2), (4) Date: Oct. 20, 2011

(87) PCT Pub. No.: WO2010/121974
PCT Pub. Date: Oct. 28, 2010

(65) Prior Publication Data
US 2012/0041236 A1    Feb. 16, 2012

(30) Foreign Application Priority Data

Apr. 22, 2009  (EP) .................................... 09158472

(51) Int. Cl.
*C01B 39/46*    (2006.01)
*C07C 209/60*   (2006.01)

(52) U.S. Cl.
USPC ........... 423/700; 423/713; 423/714; 564/485; 564/408; 564/445

(58) Field of Classification Search
None
See application file for complete search history.

(56) References Cited

U.S. PATENT DOCUMENTS

| | | |
|---|---|---|
| 4,388,288 A | 6/1983 | Dupin et al. |
| 5,114,565 A | 5/1992 | Zones et al. |
| 5,744,667 A | 4/1998 | Pellet |
| 6,143,934 A | 11/2000 | Dingerdissen et al. |
| 2004/0192970 A1 | 9/2004 | Sigl et al. |
| 2010/0174117 A1 | 7/2010 | Heidemann et al. |

FOREIGN PATENT DOCUMENTS

| | | |
|---|---|---|
| EP | A 132 736 | 2/1985 |
| EP | A 752 409 | 1/1997 |
| EP | A 822 179 | 2/1998 |
| EP | 1462165 A1 | 9/2004 |
| WO | WO-A-92/20446 | 11/1992 |
| WO | WO-97/07088 A1 | 2/1997 |
| WO | WO-02/00597 | 1/2002 |
| WO | WO-2009/124924 A1 | 10/2009 |

OTHER PUBLICATIONS

Database CAPLUS on STN, Acc. No. 2002:100471, Dimitrova et al., Reaction Kinetics and Catalysis Letters (2001), 74(2), p. 353-363 (abstract).*

* cited by examiner

*Primary Examiner* — Brian J Davis
(74) *Attorney, Agent, or Firm* — Novak Druce Connolly Bove + Quigg LLP

(57) ABSTRACT

The present invention relates to a hydroamination catalyst comprising boron beta zeolites, wherein the hydroamination catalyst is doped with lithium, and also a process for producing it. The present patent application further relates to a process for preparing amines by reaction of ammonia or primary or secondary amines with olefins at elevated temperatures and pressures in the presence of the hydroamination catalyst of the invention.

9 Claims, No Drawings

CATALYSTS AND METHOD FOR THE HYDROAMINATION OF OLEFINS

CROSS-REFERENCE TO RELATED APPLICATIONS

This application is a national stage application (under 35 U.S.C. §371) of PCT/EP2010/055078, filed Apr. 19, 2010, which claims benefit of European application 09158472.2, filed Apr. 22, 2009, the contents of each of which are incorporated herein by reference in their entireties.

FIELD OF THE INVENTION

The present invention relates to hydroamination catalysts, their production and use. The present invention further provides a process for preparing amines by hydroamination of olefins and also the use of the tertiary butylamine prepared by means of the process of the invention.

BACKGROUND

WO 97/07088 discloses a process for preparing olefins over boron beta zeolites. It is stated that the zeolites can be modified in order to increase, for example, the selectivity, the operating life or the number of possible regenerations. According to the disclosure, a possible modification of the hydroamination catalysts is to ion-exchange or dope the zeolites with alkali metals, such as Na and K, alkaline earth metals, such as Ca and Mg, earth metals, such as Tl, transition metals, such as Mn, Fe, Mo, Cu, Zn, Cr, noble metals and/or rare earth metals, such as La, Ce or Y. Doping with the element Li is not explicitly mentioned.

BRIEF SUMMARY

It is an object of the present invention to improve the yield of amines in the reaction of ammonia or primary or secondary amines with olefins, compared to the prior art.

To achieve this object we have found a hydroamination catalyst comprising boron beta zeolites which is doped with lithium.

The hydroamination catalyst of the invention comprises boron beta zeolites.

DETAILED DESCRIPTION OF THE PREFERRED EMBODIMENTS

The production of boron beta zeolites is described in the patent application WO-A-98/07088, which is incorporated by reference.

Boron beta zeolites can also be produced, for example by the method of Gaodeng Xuexiao Huaxue Xuebao (1993), 14(2), 159 to 163 or Gaodeng Xuexiao Huaxue Xuebao (1989), 10(7), 677 to 682 or WO-A-92/20446.

The hydroamination catalyst can consist entirely of boron beta zeolites.

The hydroamination catalysts of the invention usually further comprise binders which are necessary for producing shaped catalyst bodies.

The hydroamination catalysts can comprise further auxiliaries such as pore formers and pasting agents in addition to binders.

The proportion of boron beta zeolites in the hydroamination catalyst used is preferably from 10 to 100% by weight, preferably from 25 to 99% by weight and particularly preferably from 40 to 98% by weight based on the mass of the dried and calcined hydroamination catalyst.

The hydroamination catalysts can be used in the form of powder or preferably in the form of shaped bodies such as extrudates, pellets or crushed material.

Customary processes for producing shaped bodies are, for example, extrusion, tableting, i.e. mechanical pressing or pelletization, i.e. compaction by means of circular and/or rotary movements, and are described, for example, in Ertl, Knözinger, Weitkamp: "Handbook of heterogeneous catalysis", VCH Weinheim, 1997, pages 98 ff or U.S. Pat. No. 4,388,288.

To produce the shaped bodies (shaping) it is possible to add from 2 to 60% by weight (based on the composition to be shaped) of binders. Suitable binders are various aluminum oxides, preferably boehmite, amorphous aluminosilicates having a molar $SiO_2/Al_2O_3$ ratio of from 25:75 to 95:5, silicon dioxide, preferably finely divided $SiO_2$ such as silica sols, mixtures of finely divided $SiO_2$ and finely divided $Al_2O_3$, finely divided $TiO_2$ and also clays.

The hydroamination catalysts are preferably used as extrudates having diameters of, for example, 1 to 4 mm or as pellets having a diameter of, for example from 3 to 5 mm for the hydroamination of olefins. Furthermore, the hydroamination catalysts can preferably be used as crushed material obtained by crushing of shaped catalyst bodies.

After shaping, the extrudates or pressed bodies are usually dried at from 80 to 150° C. for from 2 to 16 hours and then preferably calcined.

Calcination is generally carried out at a temperature above 400° C. so that the binder material hardens. The maximum temperature is generally limited by the stability of the boron beta zeolite which loses its crystallinity at temperatures above 550° C. Calcination is generally carried out industrially in a rotary tube at a temperature in the range from 400 to 560° C. and a residence time of from 2 to 4 hours. In the laboratory, it is usually carried out in a furnace at a temperature of from 480 to 520° C. for a period of from 2 to 32 hours.

To increase the selectivity, the operating life and the number of possible catalyst regenerations, it is possible to carry out various modifications on the hydroamination catalysts.

One possible way of modifying the hydroamination catalyst is to subject the material, shaped or unshaped, to a treatment with acids such as hydrochloric acid (HCl), hydrofluoric acid (HF), phosphoric acid ($H_3PO_4$), sulfuric acid ($H_2SO_4$), oxalic acid ($HO_2C-CO_2H$) or mixtures thereof.

The treatment with acids generally converts the boron beta zeolite into the H form.

In a particular embodiment the hydroamination catalyst is treated with hydrofluoric acid (from 0.001 to 2 molar, preferably from 0.05 to 0.5 molar) and reflux for from 1 to 3 hours before shaping. After filtering off and washing, it is generally dried at from 100 to 160° C. and calcined at from 400 to 550° C.

A further particular embodiment comprises HCl treatment of the heterogeneous catalysts after shaping with binder. Here, the hydroamination catalyst is generally treated with a 3-25% strength, in particular a 12-20% strength, hydrochloric acid at temperatures in the range from 60 to 80° C. for from 1 to 3 hours, subsequently washed, dried at from 100 to 160° C. and calcined at from 400 to 550° C.

Another possible way of modifying the hydroamination catalyst is exchange with ammonium salts, for example with $NH_4Cl$, or with monoamines, diamines or polyamines, in which the boron beta zeolite is generally converted into the ammonium form. Here, the hydroamination catalyst which has been shaped with binder is generally exchanged continuously with 10-25% strength, preferably about 20% strength, NH$_4$Cl solution at from 60 to 80° C. for 2 hours at a weight ratio of hydroamination catalyst/ammonium chloride solution of 1:15 and then dried at from 100 to 120° C.

The hydroamination catalyst of the invention is doped with lithium.

Doping is preferably effected by bringing the unshaped or shaped hydroamination catalyst comprising boron beta zeolites into contact with a liquid comprising Li ions.

The liquid used is generally a liquid which is able to solvate a source of lithium ions.

Preferred liquids are water and polar organic solvents, such as alcohols, for example methanol, ethanol or isopropanol, ethers, for example THF, DMF, DMSO or NMP. In a particularly preferred embodiment, the liquid is water.

As a source of lithium ions, preference is given to using a soluble lithium salt or a lithium compound which forms Li ions in the liquid used. Particular preference is given to using a lithium salt which is soluble in the liquid as a source of lithium ions.

Preferred lithium salts are LiOH, Li nitrate, Li halides, such as LiCl, LiBr, LiF and LiI and Li carboxylates, such as Li oxalate, Li formate, Li acetate, Li oxalate, Li citrate. Particularly preferred lithium salts are LiOH, Li nitrate, LiCl, Li citrate and Li oxalate.

Lithium compounds which can form Li ions in a liquid are, for example, organolithium compounds, for example, aryllithium compounds or alkyllithium compounds, such as butyllithium, which, for example, reacts with water to give LiOH and butane, with LiOH forming Li ions in water.

Further lithium compounds which can form Li ions in a liquid are lithium alkoxides, such as Li methoxide, Li ethoxide or Li propoxide.

The concentration of Li ions in the liquid is preferably from 0.01 to 100 mol of Li ions per liter of liquid, preferably from 0.1 to 10 mol of Li ions per liter of liquid and particularly preferably from 0.2 to 5 mol of Li ions per liter of liquid.

In one preferred embodiment, doping of the boron beta zeolites is effected by ion exchange.

In a preferred embodiment, ion exchange is carried out by placing the boron beta zeolites in a flow tube and passing a liquid comprising Li ions over them at from 20 to 100° C.

In a further preferred embodiment, doping by ion exchange is carried out by impregnating or steeping the boron beta zeolites in aqueous or alcoholic solution. Impregnation of the boron beta zeolites can be carried out by customary methods (A. B. Stiles, Catalyst Manufacture—Laboratory and Commercial Preparations, Marcel Dekker, New York, 1983), for example by application of a solution comprising Li ions in one or more impregnation stages. Impregnation can also be carried out by moistening the support material with the impregnation solution to not more than saturation according to its liquid absorption capacity. However, impregnation can also be carried out in an excess of solution.

In the case of multiple impregnation operations, it is advantageous to dry and, if appropriate, calcine the support material between individual impregnation steps.

Such ion exchange can, for example, be carried out on the unmodified form, the H form or the ammonium form of the hydroamination catalysts.

Lithium-doped boron beta zeolites which have been obtained, for example, by ion exchange or by impregnation are generally dried and/or calcined as described above subsequent to doping.

The molar ratio of boron:lithium atoms in the hydroamination catalyst of the invention is particularly preferably from 2:1 to 50:1 and very particularly preferably from 5:1 to 20:1.

The molar ratio of boron atoms to lithium atoms can be measured by known methods of elemental analysis, for example atomic absorption spectrometry (AAS), atomic emission spectrometry (AES), X-ray fluorescence analysis (XRF) or ICP-OES (inductively coupled plasma optical emission spectrometry).

The hydroamination catalysts of the invention are preferably used in a process for preparing amines by reaction of ammonia or primary or secondary amines with olefins at elevated temperatures and pressures. The catalysts of the invention are very particularly preferably used in a process for preparing tert-butylamine.

The present patent application therefore further provides a process for preparing amines by reaction of ammonia or primary or secondary amines with olefins at elevated temperatures and pressures in the presence of boron beta zeolites doped with Li.

Boron beta zeolites doped with Li can be produced as described above.

Ammonia, primary or secondary amines are used in the process of the invention. The primary or secondary amines preferably have $C_{1-20}$-alkyl radicals, particularly preferably $C_{1-6}$-alkyl radicals, in particular methyl radicals or ethyl radicals.

Apart from ammonia, very particularly preferred amines are monomethylamine, dimethylamine, monoethylamine, diethylamine, n-butylamine, isopropylamine, diisopropylamine and di-n-butylamine. In a particularly preferred embodiment, ammonia is used.

Furthermore, olefins are used in the process of the invention.

As olefins, preference is given to using $C_{2-20}$-olefins which are aliphatic. They can be linear or branched. Preference is given to using $C_{2-12}$-olefins, in particular $C_{2-6}$-olefins. Examples of suitable olefins are ethene, propene, butene, isobutene and also 1,3-butadiene. In a particularly preferred embodiment, isobutene is used as olefin.

The reaction of ammonia, primary or secondary amines with an olefin gives a hydroamination product.

The hydroamination products which can preferably be prepared by means of the process of the invention are
starting from ethene and ammonia: monoethylamine, diethylamine and/or triethylamine,
starting from ethene and monoethylamine: diethylamine and/or triethylamine,
starting from isobutene and ammonia: tert-butylamine,
starting from 1,3-butadiene and ammonia: 1-amino-3-butene and/or 2-amino-3-butene,
starting from 1,3-butadiene and n-butylamine: (2-butenyl)-n-butylamine and/or (3-butenyl)-n-butylamine and
starting from propene and isopropylamine: diisopropylamine.

In a particularly preferred embodiment, the hydroamination product is tert-butylamine, obtained from isobutene and ammonia.

The reaction of the olefin with ammonia and/or the primary or secondary amine in the presence of a boron beta zeolite can be carried out, for example, as described in EP-A 132 736, EP-A 752 409, EP-A 822 179 and WO-A-02/00597.

The reaction can be carried out continuously, batchwise or as a semibatch process.

In general, ammonia and/or primary amine or, if appropriate, secondary amine are mixed with olefin in a molar ratio of from 1:1 to 10:1, preferably from 1:1 to 5:1, particularly preferably from 1:1 to 3:1, and reacted in the gas phase or the supercritical state in a fixed-bed or fluidized-bed reactor comprising the hydroamination catalyst of the invention at a pressure of from 40 to 700 bar abs., preferably from 200 to 300 bar abs., and a temperature of from 80 to 400° C., preferably from 230 to 320° C.

As an alternative, the reaction can be carried out in the liquid phase at a pressure of from 40 to 80 bar abs. and a temperature of from 60 to 120° C. in a solid-liquid moving bed reactor or a flow tube reactor comprising the hydroamination catalyst of the invention.

In a particular embodiment of this process, ammonia and/or the primary or secondary amine together with the olefin or the olefin mixture are fed as a mixture having a molar ratio of from 1:1 to 5:1, preferably from 1:1 to 3:1, into a fixed-bed reactor comprising the hydroamination catalyst of the invention and reacted in the gas phase or the supercritical state at a pressure of from 100 to 320 bar abs., preferably from 150 to 310 bar abs., in particular from 200 to 300 bar abs., and a temperature of from 200 to 350° C., preferably from 220 to 330° C., in particular from 230 to 320° C.

The position of the equilibrium and thus the conversion to the desired hydroamination product is highly dependent on the reaction pressure selected. A high pressure favors the addition product, but for technical and economical reasons, the pressure range up to 300 bar abs. generally represents an optimum. The selectivity of the reaction is influenced not only by parameters such as ammonia/amine excess and catalyst but also greatly by the temperature. Although the reaction rate of the addition reaction generally increases greatly with increasing temperature, selectivity-reducing secondary reactions may be promoted at the same time. In addition, a temperature increase is usually not advantageous from a thermodynamic point of view. The position of the temperature optimum with regard to conversion and selectivity is dependent on the constitution of the olefin, of the primary amine used and of the catalyst and is usually in the range from 220 to 320° C.

After the reaction, the product of the hydroamination reaction is usually separated, e.g. by distillation, rectification, filtration, scrubbing with water or adsorption.

Unreacted starting materials or inert gases introduced can be recirculated to the reaction.

The tert-butylamine prepared according to the present invention can be used as raw material in the rubber industry (vulcanization accelerator) or for the production of crop protection agents or pharmaceuticals.

The hydroamination catalysts of the invention make it possible to achieve an improvement in the yield of amines in the reaction of ammonia or primary or secondary amines with olefins compared to the prior art. The catalysts of the invention can be produced on an industrial scale and have a long operating life. The catalyst of the invention generally allows a higher space velocity over the catalyst at a given conversion or a higher conversion at a given space velocity over the catalyst.

The invention is illustrated by the following examples.

EXAMPLES

Catalyst Synthesis

Example 1

Production of a Shaped Boron Beta Zeolite Body 133 g of boron beta zeolite ($SiO_2:B_2O_3$ ratio=20, synthesized as described in WO 97/07088) were admixed with 67 g of boehmite and 4 g of formic acid. The mixture was compacted in a kneader and kneaded with careful addition of water (110 ml). The kneading time was 60 min. 2.5 mm extrudates were produced in an extruder at a pressing pressure of 100 bar, dried at 110° C. for 16 hours and subsequently calcined at 500° C. for 16 hours. The boron content of the extrudates produced in this way was 100 mmol per 100 g of extrudates, and the water absorption was 0.6 ml/g.

Example 2

Doping of the Shaped Boron Beta Zeolite Body with Li 100 g of extrudates were impregnated with a solution of 0.73 g of $LiNO_3$ (95% strength=10 mmol of Li) in 60 ml of water while rotating (20 revolutions/min) on a rotary evaporator at 20° C. After brief partial drying at 50° C. under reduced pressure, the impregnated extrudates were dried at 120° C. for 12 hours in a drying oven and subsequently calcined at 450° C. under a stream of 50 standard 1/h of air for 8 hours in a rotary tube furnace. The extrudates were subsequently crushed and a crushed material fraction having a diameter of 1-1.6 mm was sieved off.

Example 3

Doping of the Shaped Boron Beta Zeolite Body with Li

The procedure of example 1 was repeated, except that 0.36 g of $LiNO_3$ (5 mmol of Li) was used.

Example 4

Doping of the Shaped Boron Beta Zeolite Body with Li

The procedure of example 1 was repeated, except that 1.10 g of $LiNO_3$ (15 mmol of Li) were used.

Example 5

Doping of the Shaped Boron Beta Zeolite Body with Li

The procedure of example 1 was repeated, except that 1.46 g of $LiNO_3$ (20 mmol of Li) were used.

Example 6

Doping of the Shaped Boron Beta Zeolite Body with Li

The procedure of example 1 was repeated, except that 3.6 g of $LiNO_3$ (50 mmol of Li) were used.

Example 7

Doping of the Shaped Boron Beta Zeolite Body with Na

The procedure of example 1 was repeated, except that 0.85 g of $NaNO_3$ (10 mmol of Na) was used.

Example 8

Doping of the Shaped Boron Beta Zeolite Body with Na

The procedure of example 1 was repeated, except that 1.70 g of NaNO$_3$ (20 mmol of Na) were used.

Example 9

Doping of the Shaped Boron Beta Zeolite Body with Rb

The procedure of example 1 was repeated, except that 1.48 g of RbNO$_3$ (10 mmol of Rb) were used.

Example 10

Doping of the Shaped Boron Beta Zeolite Body with Cs

The procedure of example 1 was repeated, except that 1.95 g of CsNO$_3$ (10 mmol of Cs) were used.

Example 11

Doping of the Shaped Boron Beta Zeolite Body with K

The procedure of example 1 was repeated, except that 0.51 g of KNO$_3$ (5 mmol of K) was used.

Example 12

Doping of the Shaped Boron Beta Zeolite Body with K

The procedure of example 1 was repeated, except that 1.01 g of KNO$_3$ (10 mmol of K) was used.

Example 13

Doping of the Shaped Boron Beta Zeolite Body with K

The procedure of example 1 was repeated, except that 2.02 g of KNO$_3$ (20 mmol) were used.

Preparation of Tert-Butylamine 43 g/h of a mixture of isobutene and NH$_3$ (1 mol:1.5 mol) were passed over 10 g of crushed catalyst material under isothermal conditions at 270° C. and a pressure of 270 bar in a tube reactor (6 mm internal diameter) and the reaction was monitored by means of on-line GC.

The following table lists the results for catalysts as described above (examples 1 to 13) in each case after a running time of 48 h:

| Example | | Sel. tBA | Yield of tBA g of tBA/g of feed | Molar ratio of B:alkali metal in the hydroamination catalyst |
|---|---|---|---|---|
| 1 | B-Beta | >99% | 14.0 | — |
| 2 | 10 mmol Li | >99% | 15.0 | 10:1 |
| 3 | 5 mmol Li | >99% | 15.1 | 20:1 |
| 4 | 15 mmol Li | >99% | 15.0 | 20:3 |
| 5 | 20 mmol Li | >99% | 14.9 | 5:1 |
| 6 | 50 mmol Li | >99% | 13.2 | 2:1 |
| 7 | 10 mmol Na | >99% | 14.5 | 10:1 |
| 8 | 20 mmol Na | >99% | 14.3 | 5:1 |
| 9 | 10 mmol Rb | >99% | 14.3 | 10:1 |
| 10 | 10 mmol Cs | >99% | 14.1 | 10:1 |
| 11 | 5 mmol K | >99% | 13.9 | 20:1 |
| 12 | 10 mmol K | >99% | 14.5 | 10:1 |
| 13 | 20 mmol K | >99% | 13.7 | 5:1 |

It can be seen that doping with the alkali metals Na, K, Rb, Cs leads to no increase or only a slight increase in yield of maximum 0.5% compared to using undoped B-Beta while an increase in yield by 0.9-1.1% can be achieved by doping with Li.

The invention claimed is:

1. A hydroamination catalyst comprising boron beta zeolites wherein the hydroamination catalyst is doped with lithium and the molar ratio of boron to lithium atoms in the hydroamination catalyst is from 5:1 to 50:1.

2. The hydroamination catalyst according to claim 1, wherein doping is effected by bringing the hydroamination catalyst into contact with a liquid comprising Li ions.

3. The hydroamination catalyst according to claim 2, wherein the concentration of Li ions in the liquid is from 0.01 to 100 mol of Li ions per liter of liquid.

4. The hydroamination catalyst according to claim 1, wherein doping is effected by ion exchange or impregnation.

5. The hydroamination catalyst according to claim 1, wherein the proportion of boron beta zeolites in the hydroamination catalyst is from 10 to 100% by weight.

6. A process for preparing amines by reaction of ammonia or primary or secondary amines with olefins at elevated temperatures and pressures in the presence of a hydroamination catalyst according to claim 1.

7. The process according to claim 6, wherein the molar ratio of ammonia, primary or secondary amines to olefin is in the range from 1:1 to 3:1.

8. The process according to claim 6, wherein olefins are reacted with ammonia.

9. The process according to claim 6, wherein isobutene is used as olefin.

* * * * *